United States Patent [19]

Barbero et al.

[11] Patent Number: 4,743,404
[45] Date of Patent: May 10, 1988

[54] PROCESS FOR PREPARING ALKYL-SULPHONYL CHLORIDES AND ARYLALKYL-SULPHONYL CHLORIDES

[75] Inventors: Margherita Barbero, Bra; Iacopo Degani, Turin; Rita Fochi, Turin; Valeria Regondi, Turin, all of Italy

[73] Assignee: Consiglio Nazionale Delle Ricerche, Rome, Italy

[21] Appl. No.: 4,413

[22] Filed: Jan. 20, 1987

[30] Foreign Application Priority Data

Jan. 24, 1986 [IT] Italy ................................ 19179 A/86

[51] Int. Cl.$^4$ ............................................. C07C 143/70
[52] U.S. Cl. ................................ 260/543 R; 260/543 H
[58] Field of Search ........................ 260/543 R, 543 H

[56] References Cited

U.S. PATENT DOCUMENTS

| | | | |
|---|---|---|---|
| 3,544,625 | 12/1970 | Masat | 260/543 H |
| 3,878,248 | 4/1975 | Phillips | 260/543 H |
| 4,093,651 | 6/1978 | Honig et al. | 260/543 H |

FOREIGN PATENT DOCUMENTS

| | | | |
|---|---|---|---|
| 508163 | 12/1954 | Canada | 260/543 H |
| 2144876 | 3/1973 | Fed. Rep. of Germany | 260/543 R |
| 5102555 | 8/1980 | Japan | 260/543 R |

*Primary Examiner*—Paul J. Killos
*Attorney, Agent, or Firm*—Young & Thompson

[57] ABSTRACT

Process for preparing alkyl-sulphonyl chlorides and arylalkyl-sulphonyl chlorides of formula $RSO_2Cl$ (R being alkyl or arylalkyl), starting from S,S-dialkyl or diarylalkyl dithiocarbonates RS—CO—SR, consisting in reacting the starting compound with gaseous chlorine in the presence of water, at $0°$–$+10°$ C.

4 Claims, No Drawings

PROCESS FOR PREPARING ALKYL-SULPHONYL CHLORIDES AND ARYLALKYL-SULPHONYL CHLORIDES

BACKGROUND OF THE INVENTION

There are known to be several compounds belonging to the class of alkyl-sulphonyl chlorides and arylalkyl-sulphonyl chlorides, which find a great number of applications as intermediates or catalysts in organic syntheses, as additives and intermediates for the oil industry, as auxiliaries for the textile industry, as additives for the rubber industry, as pesticides and, particularly, as additives for the tanning industry, and this is due to the high reactivity of the sulphonyl chloride group —SO$_2$Cl.

Sulphonyl chlorides can be prepared by direct sulphochlorination of the corresponding hydrocarbons with various reactants such as, for example, mixtures of Cl$_2$+SO$_2$ or sulphuryl chloride SO$_2$Cl$_2$, and in many cases the reaction is activated with actinic radiations. These methods generally give good results for the first terms of the series, as methan-sulphonyl chloride and ethan-sulphonyl chloride; whereas they give unsatisfactory results for preparing higher terms, due to the forming of mono-, di- and polysulphonyl chlorides, and also by-products as unsaturated chlorides and hydrocarbons, which give rise to very complex mixtures from which the pure compounds are difficult to separate.

There are also known to be methods for preparing sulphonyl chlorides having a defined structure, based on the oxidation-chlorination—carried out with gaseous chlorine in the presence of water—of sulpho-organic compounds belonging to various functional classes, as mercaptans, disulphides, thiocyanates, isothiouronium salts, Bunte salts and others. In the case of using dimethyl disulphide as a starting compound, methan-sulphonyl chloride can be easily obtained, with excellent yields, through the reaction:

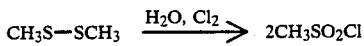

Nevertheless, in general, the other alkyl-disulphides and the other sulpho-organic compounds are of difficult and too costly preparation, or else they supply the corresponding sulphonyl chlorides in preparatively and thus economically unacceptable yields, and this mainly in the case of higher terms.

SUMMARY OF THE INVENTION

It has now been found that alkyl- or arylalkyl-sulphonyl chlorides can be obtained with high yields and with a high selectivity, by action of gaseous chlorine on S,S-dialkyl or S,S-diarylalkyl dithiocarbonates in the presence of water, at a temperature between 0° and +10° C.

DESCRIPTION OF THE PREFERRED EMBODIMENTS

The reaction can be represented as follows:

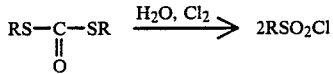

wherein R is an alkyl or arylalkyl. The yield is very high, generally higher than 90%. The HCl formed in the reaction creates no problems as far as separation, as it remains in the aqueous phase. The reaction is completed in about 60 l to 90 minutes. Sulphonyl chloride can be easily separated from the aqueous reaction phase by filtering, or by extraction with an extractant (for example: CCl$_4$, CHCl$_3$, etc.).

The dithiocarbonates used as primary substance in the process according to the invention are known products. An advantageous process to obtain the same is described in "Synthesis" (1978) n. 5, 365–68, and "Synthesis" (1981) n. 2, 149–51.

As a primary substance, economic products are used, such as CS$_2$, alcohol ROH and an halide RX (X being halogen, R being alkyl or arylalkyl), with the reaction:

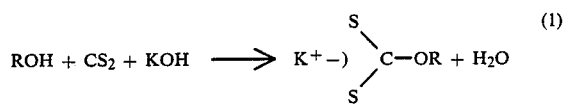

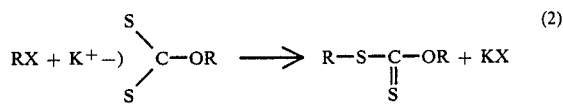

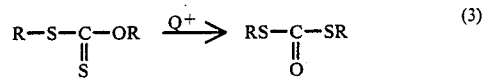

wherein Q$^+$ is ammonium or phosphonium quaternary salt.

In the aforespecified process, a sulphonic ester RSO$_2$OR can be advantageously used as an alkylating agent instead of halide RX.

Said sulphonic ester can in turn be very simply obtained from a sulphonyl chloride RSO$_2$Cl, obtained according to the process of the present invention, by reaction with an alcohol ROH.

The reaction (2) will thus be:

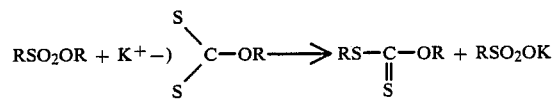

The process in its whole, starting from xanthogenate, can be thus represented by the reactions:

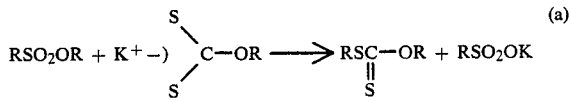

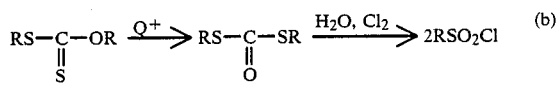

It here results, in practice, that the primary substances are only potassium xanthogenate, alcohol ROH and chlorine.

Evidently, said process is particularly advantageous when sulphonyl chloride is being prepared as an intermediate to obtain, as final product, sulphonic acid RSO$_2$OH or its salts.

A practical embodiment to carry out the process for preparing sulphonyl chlorides is illustrated in the following example, which should by no means be considered as limiting the present invention.

EXAMPLE

The method used consists in dispersing S,S-dialkyl or S,S-diarylalkyl dithiocarbonate (0,05 moles) into water (30 ml), and in bringing the mixture to 0°+5° C. by cooling in an ice bath and keeping it well stirred. A gaseous chlorine flow is then introduced into the aqueous dispertion, regulating the absorption of chlorine so as to keep the temperature between +5° and +10° C.

According to the product being treated, 60 to 90 minutes are required for completing the reaction.

The sulphonyl chlorides thus obtained have been separated from the aqueous phase by filtering or extraction with an extractant (for example: $CCl_4$, $CHCl_3$, etc.).

It has thus been possible to obtain the sulphonyl chlorides listed hereunder, with the specified yields:

| | | | | |
|---|---|---|---|---|
| $CH_3$—$SO_2Cl$ | yield | 75:85% | p.e. | 62–63° C./17 mm Hg |
| $C_2H_5$—$SO_2Cl$ | yield | 95% | p.e. | 74–75° C./17 mm Hg |
| $C_4H_9$—$SO_2Cl$ | yield | 93% | p.e. | 97–98° C./17 mm Hg |
| $C_8H_{17}$—$SO_2Cl$ | yield | 94% | p.e. | 145–146° C./17 mm Hg |
| $C_{12}H_{25}$—$SO_2Cl$ | yield | quantitative | p.f. | 40–41° C. |
| $C_{16}H_{33}$—$SO_2Cl$ | yield | quantitative | p.f. | 57–58° C. |
| $C_{18}H_{37}$—$SO_2Cl$ | yield | quantitative | p.f. | 63–64° C. |
| $C_6H_5CH_2$—$SO_2Cl$ | yield | 96% | p.f. | 91–92° C. |
| 4Cl—$C_6H_4$—$CH_2$—$SO_2Cl$ | yield | 96% | p.f. | 96° C. |

We claim:

1. Process for preparing sulphonyl chlorides of formula $RSO_2Cl$, wherein R is alkyl or arylalkyl, characterized in that gaseous chlorine is introduced into an aqueous dispersion of a dithiocarbonate of formula

wherein R is as specified above, kept at a temperature of between 0° and +10° C.

2. Process according to claim 1, wherein the sulphonyl chloride is separated from the aqueous phase of reaction by filtering.

3. Process for preparing a sulphonyl chloride $RSO_2Cl$ according to claim 1, also characterized in that the starting dithiocarbonate

is prepared from potassium xanthogenate

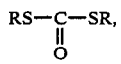

by reaction with sulphonic ester $RSO_2OR$ as an alkylating agent, said sulphonic ester having been obtained from the corresponding sulphonyl chloride $RSO_2Cl$ by alcoholysis with ROH.

4. Process according to claim 1, wherein the sulphonyl chloride is separated from the aqueous phase of reaction by extraction with an extractant.

* * * * *